United States Patent [19]

Palynchuk

[11] Patent Number: 5,097,710
[45] Date of Patent: Mar. 24, 1992

[54] ULTRASONIC FLASH GAUGE

[76] Inventor: Alexander Palynchuk, 9940-112 St., Edmonton, Alberta, Canada, T5K 1L7

[21] Appl. No.: 99,718

[22] Filed: Sep. 22, 1987

[51] Int. Cl.⁵ .......................................... G01N 29/00
[52] U.S. Cl. .................................................... 73/644
[58] Field of Search ................. 73/588, 618, 620, 621, 73/622, 633, 634, 637, 644, 638; 91/361, 362

[56] References Cited

U.S. PATENT DOCUMENTS

| | | | |
|---|---|---|---|
| 2,751,783 | 6/1956 | Erdman | 73/634 |
| 3,233,449 | 2/1966 | Harmon | 73/622 |
| 3,326,037 | 6/1967 | Stewart | 73/620 |
| 3,575,042 | 4/1971 | Lovelace | 73/620 |
| 3,670,562 | 6/1972 | Muto et al. | 73/634 |
| 3,673,860 | 7/1972 | Flaherty et al. | 73/620 |
| 4,336,745 | 6/1982 | Lund | 91/361 |
| 4,416,187 | 11/1983 | Nyström | 91/361 |
| 4,423,636 | 1/1984 | Plante | 73/622 |
| 4,437,332 | 3/1984 | Pittaro | 73/644 |
| 4,472,975 | 9/1984 | Beck et al. | 73/622 |
| 4,507,969 | 4/1985 | Djordjevic et al. | 73/644 |
| 4,513,782 | 4/1985 | Contartese et al. | 91/361 |
| 4,558,598 | 12/1985 | Young | 73/644 |
| 4,587,849 | 5/1986 | Gross | 73/644 |
| 4,749,936 | 6/1988 | Taplin | 91/361 |
| 4,757,747 | 8/1988 | Blatter et al. | 91/362 |

FOREIGN PATENT DOCUMENTS 54-21372 2/1979 Japan.
55-75607 7/1980 Japan.

OTHER PUBLICATIONS

Krautkramer et al., "Ultrasonic Testing of Materials", 2nd Ed. (1977), p. 202.
Western Instruments, A Palynchuk Company, "Responding to the Welded Tube Industry's Greatest Technological Need . . . ", Apr. 1976.

Primary Examiner—Hezron E. Williams
Assistant Examiner—Louis M. Arana
Attorney, Agent, or Firm—Foley & Lardner

[57] ABSTRACT

An ultrasonic flash gauge is disclosed that provides a profile of a weld area in order to determine inside flash conditions in a pipe. The flash gauge is capable of operating at high temperature conditions adjacent to a electric resistance welder, thereby permitting real time control of the inside flash trimming operation. A focused ultrasonic transducer is employed in order to obtain the resolution required for detecting the profile of the flash. The flash gauge is constructed to uniformly maintain a water column between the transducer and the pipe surface to prevent boiling or air bubble entrapment which would interfere with the operation of the transducer.

29 Claims, 17 Drawing Sheets

WELD POINT
WELDED SEAM
SLIDING CONTACTS
HIGH-FREQUENCY CURRENT ENTERS TUBE VIA SLIDING CONTACTS AND FLOWS ALONG VEE EDGES TO AND FROM WELD POINT

TYPICAL INSIDE AND OUTSIDE FLASH

SCREEN DISPLAY FOR FIG. 16a

UNDERCUT

SCREEN DISPLAY FOR FIG. 17a

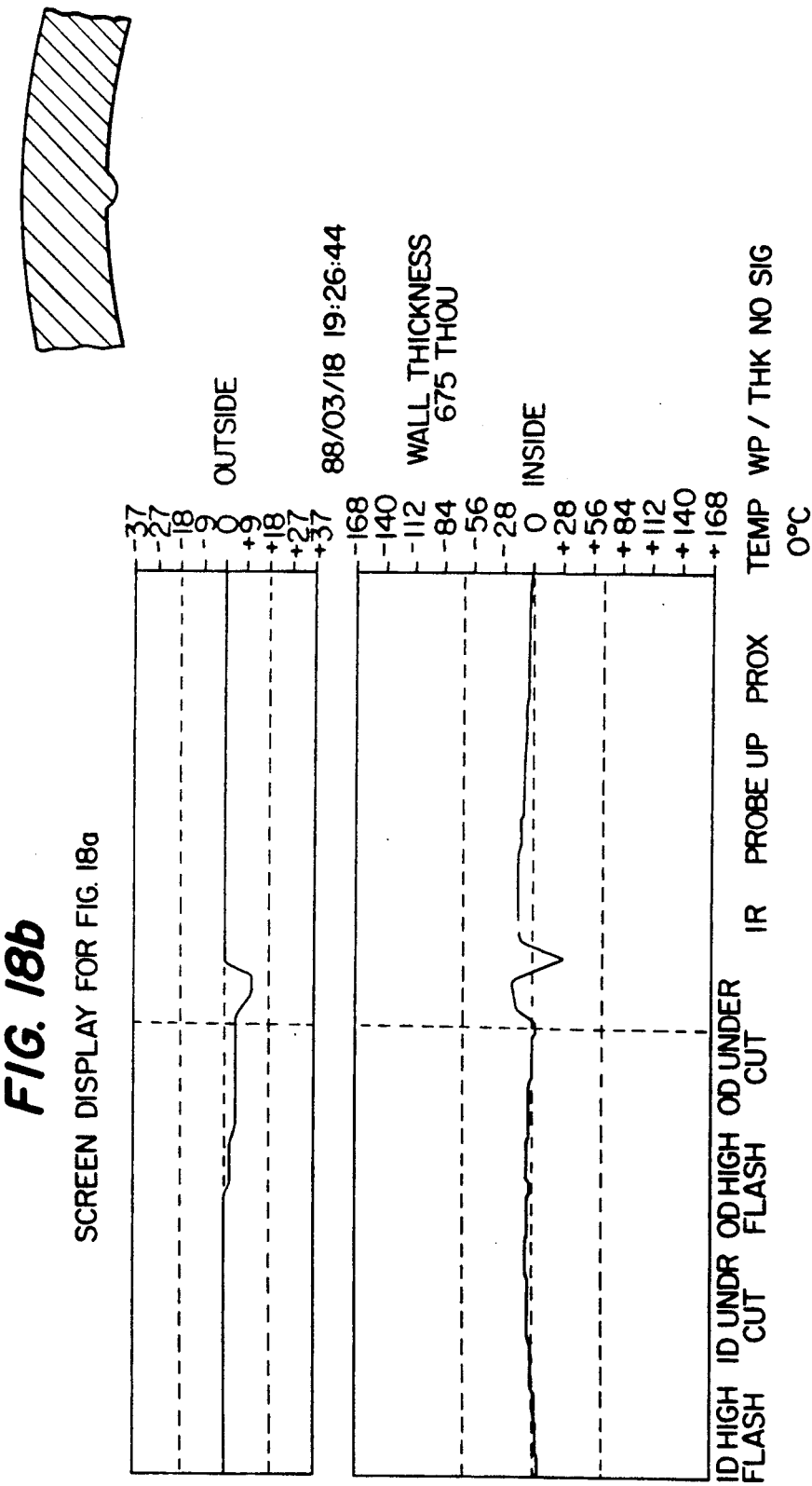

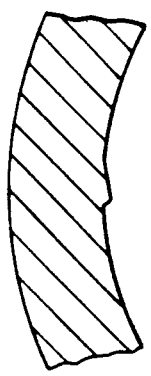
FIG. 19a CHIPPED INSIDE TRIM TOOL
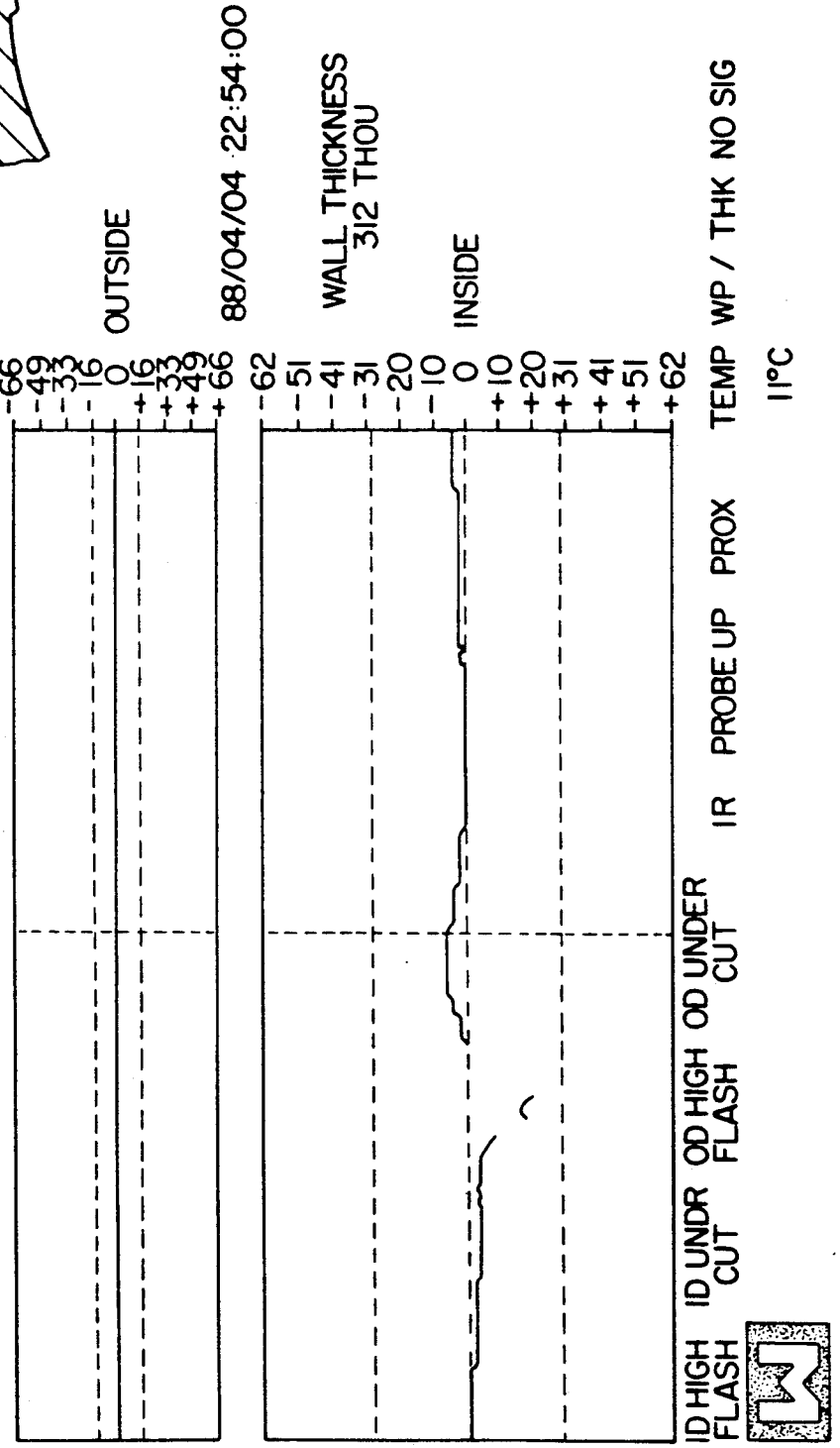
FIG. 19b SCREEN DISPLAY FOR FIG. 19a

LOCATION OF FLASH GAUGE AT MILL

ULTRASONIC FLASH GAUGE

BACKGROUND OF THE INVENTION

The invention is related to the field of ultrasonic non-destructive testing. In particular, the invention relates to an apparatus for measuring "inside" flash found in welded pipes.

Electric resistance welding (ERW) has become the most popular and proven method available for the manufacture of pipe. The ERW process, which includes radio frequency contact, radio frequency induction, low frequency resistance, and D.C. resistance welding, is a forge welding process in which the edges of a metal strip are heated by electric current flow. As shown in FIG. 1, high frequency current enters the tube via sliding contacts and flows along the edges of the metal strip to and from the weld point. The heated edges of the metal strip (or skelp) are forged welded together resulting in protrusions, most commonly referred to as flash, on both the inside and outside of the formed pipe (See FIG. 2).

Outside flash is generally removed by a tungsten carbide cutting tool contoured to the pipe surface. The effectiveness of the outside flash removal process may easily be ascertained and controlled, as outside flash is readily visible.

Inside flash is removed using a trim tool that is positioned at point inside the pipe past the weld point. The trim tool is anchored by a support structure at a point where the edges of the metal strip are still separated. The specifications for inside trim conditions vary with various types and grades of products, but generally call for adherence to tolerances as small as 0.001 of an inch. For some applications complete and clean removal of flash is generally accomplished by undercutting as shown in FIG. 3. such as for drawn over mandrel (DOM) process. Although it is important to have adequate undercut to ensure clean flash removal, excess undercut must be avoided as it cannot be tolerated in successive drawing processes. An excess of remaining flash is undesirable, for example, in line pipe, as the flash can damage pipeline pigs used for both cleaning and the introduction of corrosion control agents. Remaining amounts of flash can also act as crevices that may trap corrosive products. It will be readily understood that the detection and control of inside flash is difficult due to its location within the pipe. In fact, the condition of the inside flash in conventional tube operations is indeterminable until the pipe can be inspected after a downstream cut off operation. As a result, a great deal of scrap pipe can be generated if a condition, such as the misalignment of the trim tool, results in an out of tolerance condition of the inside flash. An apparatus capable of monitoring the condition of inside flash at a point near the welding process could significantly improve the pipe production process by permitting realtime correction of out of tolerance inside flash conditions.

To date, attempts to produce an apparatus capable of non-destructive monitoring of inside flash have met with little success. Specifically, efforts to employ conventional ultrasonic flaw detection systems, such as shear testing systems, have been found unsatisfactory for the detection and monitoring of inside flash. Two major problems have been encountered; the inability of conventional ultrasonic systems to detect with accuracy the presence of inside flash even in static conditions, and the difficulty in locating an ultrasonic system, which employs a water column to provide coupling between an ultrasonic sensor and the pipe, in close proximity to a weld point having a temperature of approximately 1500 degrees fahrenheit. Specifically, with respect to the latter problem, the high temperature of the weld point causes the water to boil thereby creating bubbles that interfere with the ultrasonic signal.

In addition, the structural requirements for such an apparatus are further complicated by the requirement of rapid transverse motion of the ultrasonic sensor across the weld line. The transverse motion is required to generate a weld profile, however, such motion is counter-active to the requirement of accurate positioning of the sensor in order to detect the extremely small inside flash variation.

SUMMARY OF THE INVENTION

An object of the invention is to provide an apparatus capable of non-destructive detection and monitoring of inside flash.

Another object of the invention is to provide an apparatus for the detection of inside flash that can be located in close proximity to a weld point in a pipe production line.

A further object of the invention is to provide an apparatus for the detection of inside flash that is capable of determining the wall thickness of the pipe and the thickness of the inside flash.

A still further object of the invention is to provide an apparatus for the detection of inside flash that employs an ultrasonic sensor, and prevents the formation of steam bubbles in the water column employed to couple the ultrasonic sensor to the pipe.

An additional object of the invention is to provide an apparatus for the detection of inside flash that provides rapid translational movement of the ultrasonic sensor in a direction transverse to the weld line while maintaining accurate positional stability.

These and other objects are accomplished according to the invention, by an apparatus comprising:

a. a probe unit having a focused ultrasonic transducer, for generating a signal indicative of the thickness of a weld point on a material to be tested, said transducer being spaced from said weld point by a water column, and said probe unit being constructed to maintain said water column uniformly to prevent interference with the operation of said focused ultrasonic transducer;

b. a positioning unit for maintaining the horizontal and vertical position of said probe unit relative to said weld point; c. a control unit for controlling the operation of said probe unit and for displaying the signal generated by said probe unit.

The present invention overcomes the problems previously experienced in attempts to provide an apparatus capable of detecting inside flash, by employing a focused ultrasonic sensor having a resolution capable of detecting the extremely thin inside flash. The focused ultrasonic sensor is incorporated in a probe unit that employs a shoe which rides on the surface of the pipe to be monitored. The structure of the shoe is uniquely formed to prevent the boiling of a water column that is passed between the shoe and the pipe. The probe unit may therefore be placed in close proximity to the welding point, thereby permitting realtime monitoring of the inside flash condition.

BRIEF DESCRIPTION OF THE DRAWINGS

With the above as background, reference should now be made to the following figures for a detailed description of the invention:

FIGS. 16a-b, 17a-b, 18a-b, 19a-b illustrate typical profiles of a weld point and simulated displays of the output from the flash gauge shown in FIG. 4;

DETAILED DESCRIPTION OF THE PREFERRED EMBODIMENTS

Figure 1:
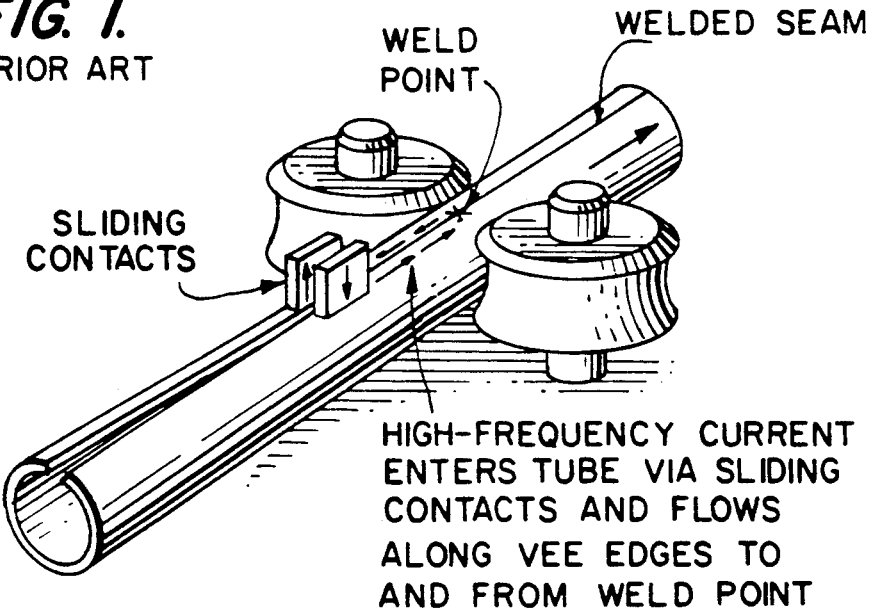
FIG. 1 illustrates a typical electric resistance welding operation.
Figure 2:
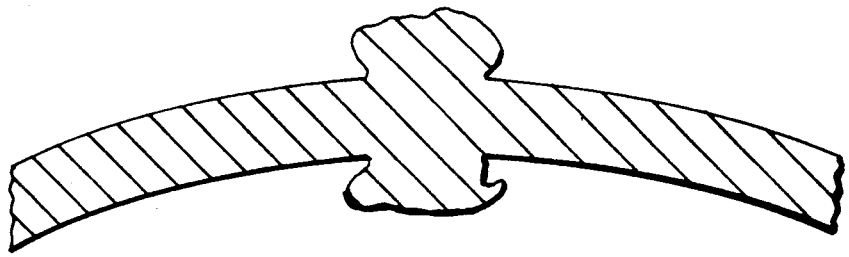
FIG. 2 illustrates a cross section of a weld point in a pipe showing a typical inside and outside flash condition.
Figure 3:
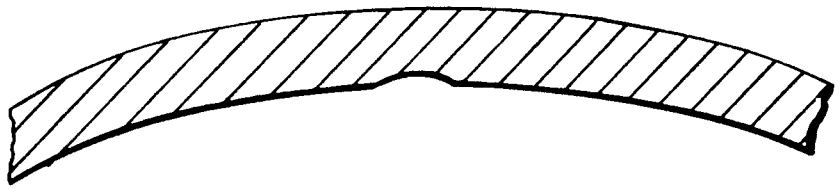
FIG. 3 illustrates a cross section of a pipe having an undercut to remove inside flash.
Figure 4:
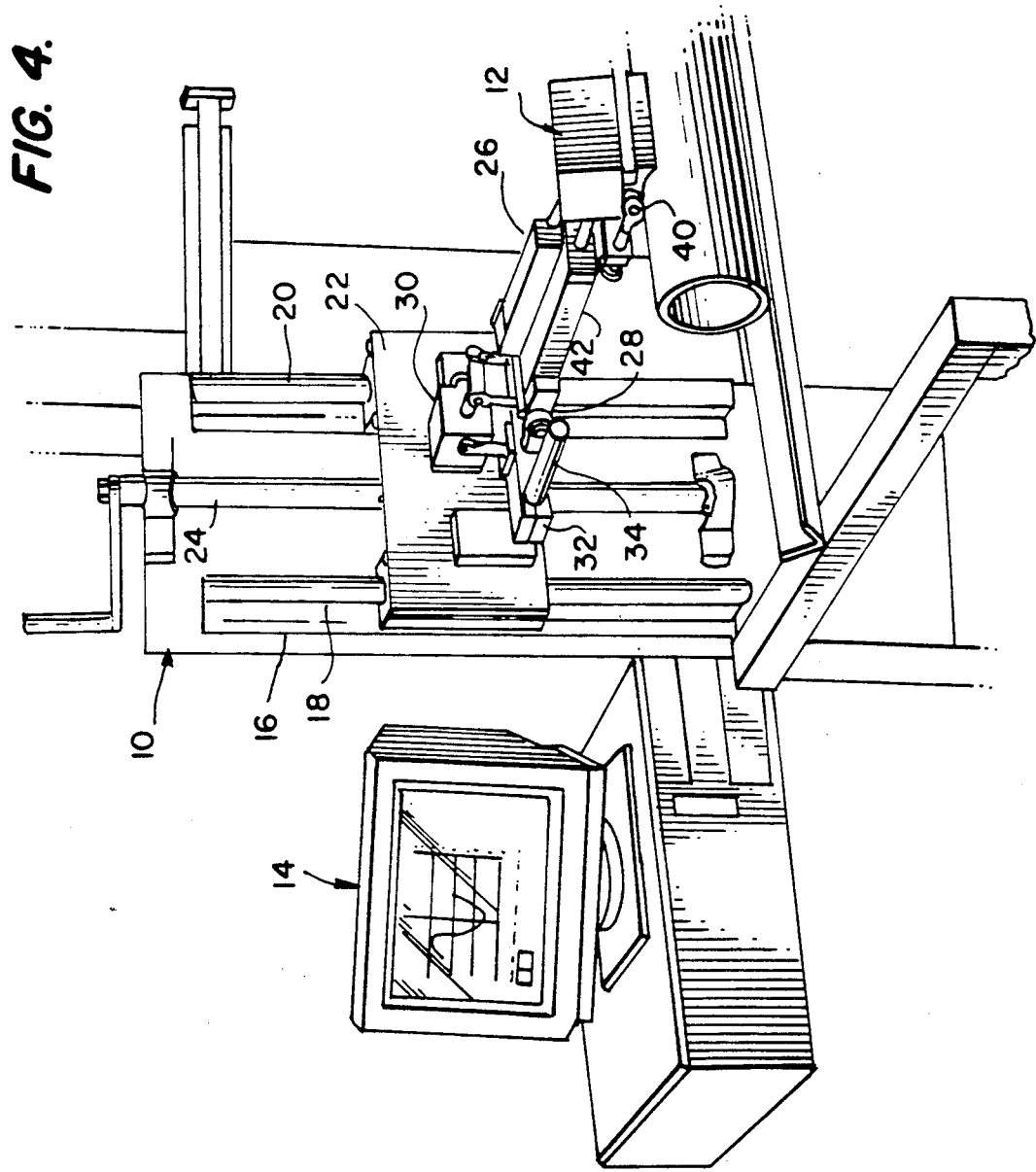
FIG. 4 is a perspective view of a flash gauge according to the present invention.
Figure 5:
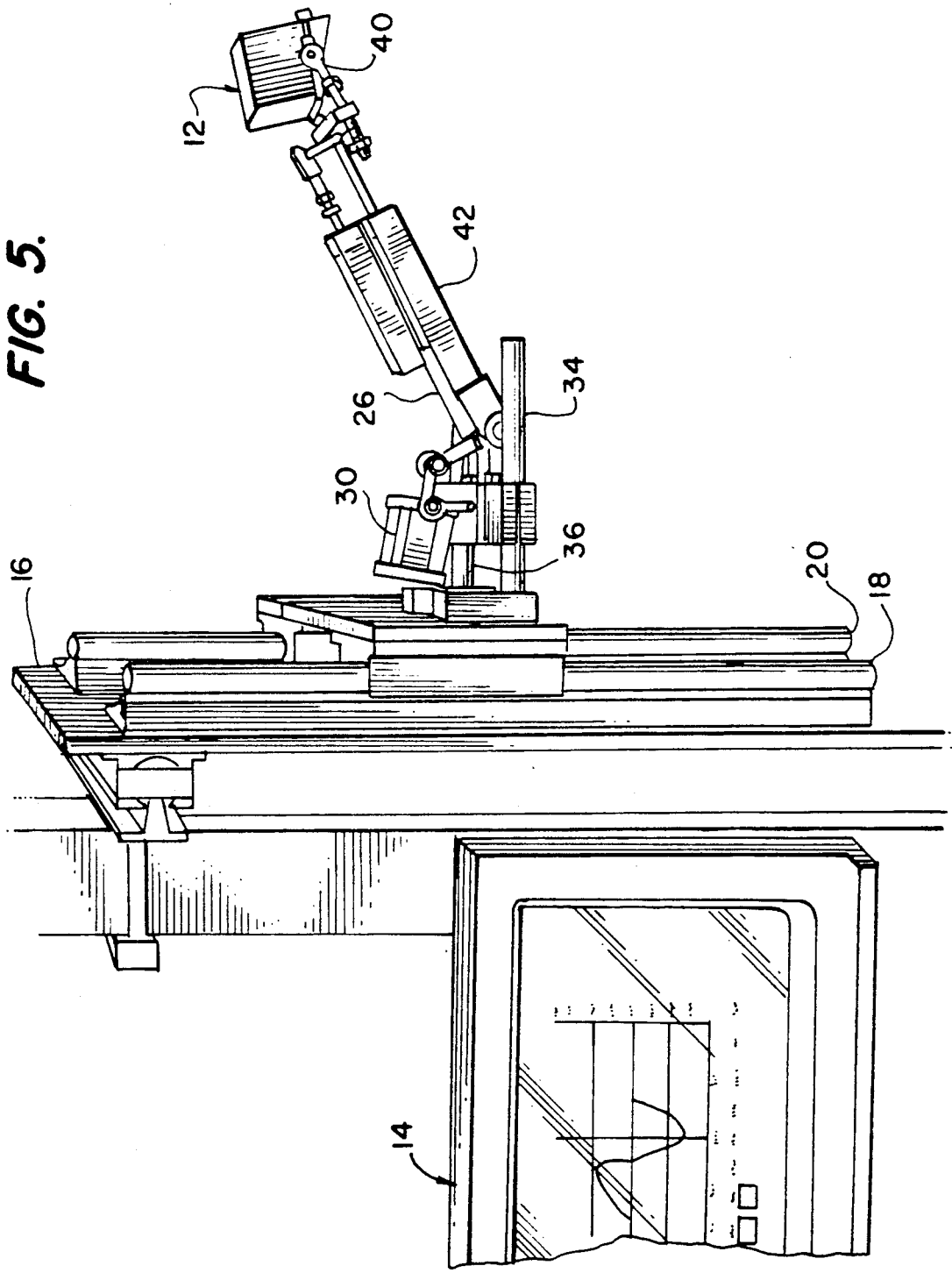
FIG. 5 illustrates the control arm of the flash gauge shown in FIG. 4 in the raised position.

Referring now to FIG. 4, an ultrasonic flash gauge according to the present invention is shown having a positioning unit 10, and a probe unit 12 that is electrically connected to a control unit 14. The positioning unit 10 consists of a support structure 16, having guide rails 18 and 20 to which a mounting plate 22 is movably attached. The mounting plate 22 is also coupled to a vertical adjustment screw 24 that is used to control the vertical position of the mounting plate 22. A control arm 26 is rotatably coupled to a horizontal adjustment plate 32 via a pivot connection 28 that permits the control arm 26 to be raised from the horizontal position when a pneumatic linear actuator 30, attached to the horizontal adjustment plate 32, is activated (See FIG. 5). The linear actuator 30 applies a controlled downward force to the control arm 26 to which the probe unit 12 is attached. The horizontal adjustment plate 32 is movably mounted on guide rails 34 and 36 which are in turn coupled to the mounting plate 22. The position of the horizontal adjustment plate 32 can be varied along the guide rails 34 and 36 thereby providing horizontal adjustment of the control arm 26. The probe unit 12 is coupled to the control arm 26 via a pivot coupling 40 that permits the probe unit 12 to follow the contour of the pipe being tested when a linear actuator 42 in the control arm 26 is activated.

Figure 6:
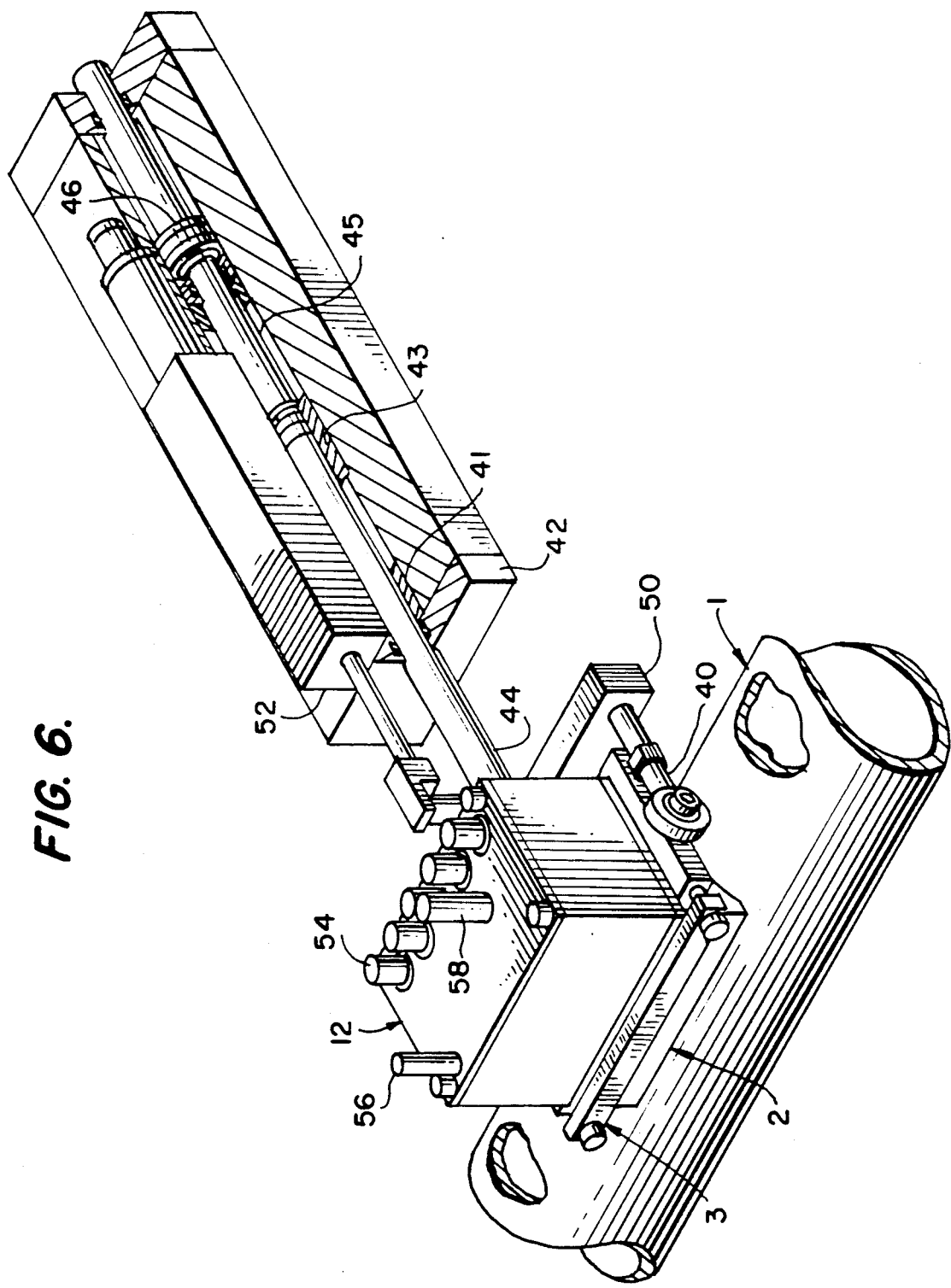
FIG. 6 is a partial cross sectional view of the control arm shown in FIG. 4.

The structure of the control arm 26 and probe unit 12 is shown in more detail in FIG. 6. The linear actuator 42 consists of a rod 44 coupled rotatably via a ball bearing joint 43 to a second rod 45 of a pneumatic actuator which in turn is connected to the piston 46 of the pneumatic actuator. Bearings 41 are provided so that the rod 44 may move rotatably, as well as axially providing fully gimbled movement for the probe unit 12. The rod 44 is connected to a bracket 50 which holds the pivot coupling 40 that is attached to the probe unit 12. A linear transducer 52 is connected to the bracket 50 to provide positional information to a solenoid valve control circuit (not shown). The solenoid valve control circuit controls the operation of a solenoid switching valve (not shown) that alternately switches air pressure between different portions of the piston cylinder of the pneumatic actuator in order to cause oscillatory motion of the rod 44. The structure of the control arm 26 permits the transverse movement of the probe unit 12 relative to the weld line while maintaining a high degree of positional accuracy. The stability of the control arm 26 is critical as the sensor unit 12 is measuring the thickness of the pipe to a resolution of up to 0.001 of an inch. Any instability in the control arm 26 would result in invalid data from the probe unit 12. The probe unit 12 contains an ultrasonic transducer along with necessary probe control circuitry. Connectors 54 are provided on the top surface of the probe unit 12 to provide electrical connection to the control unit 14, along with primary water inlet tube 58, and a secondary water inlet tube 56.

Figure 7:
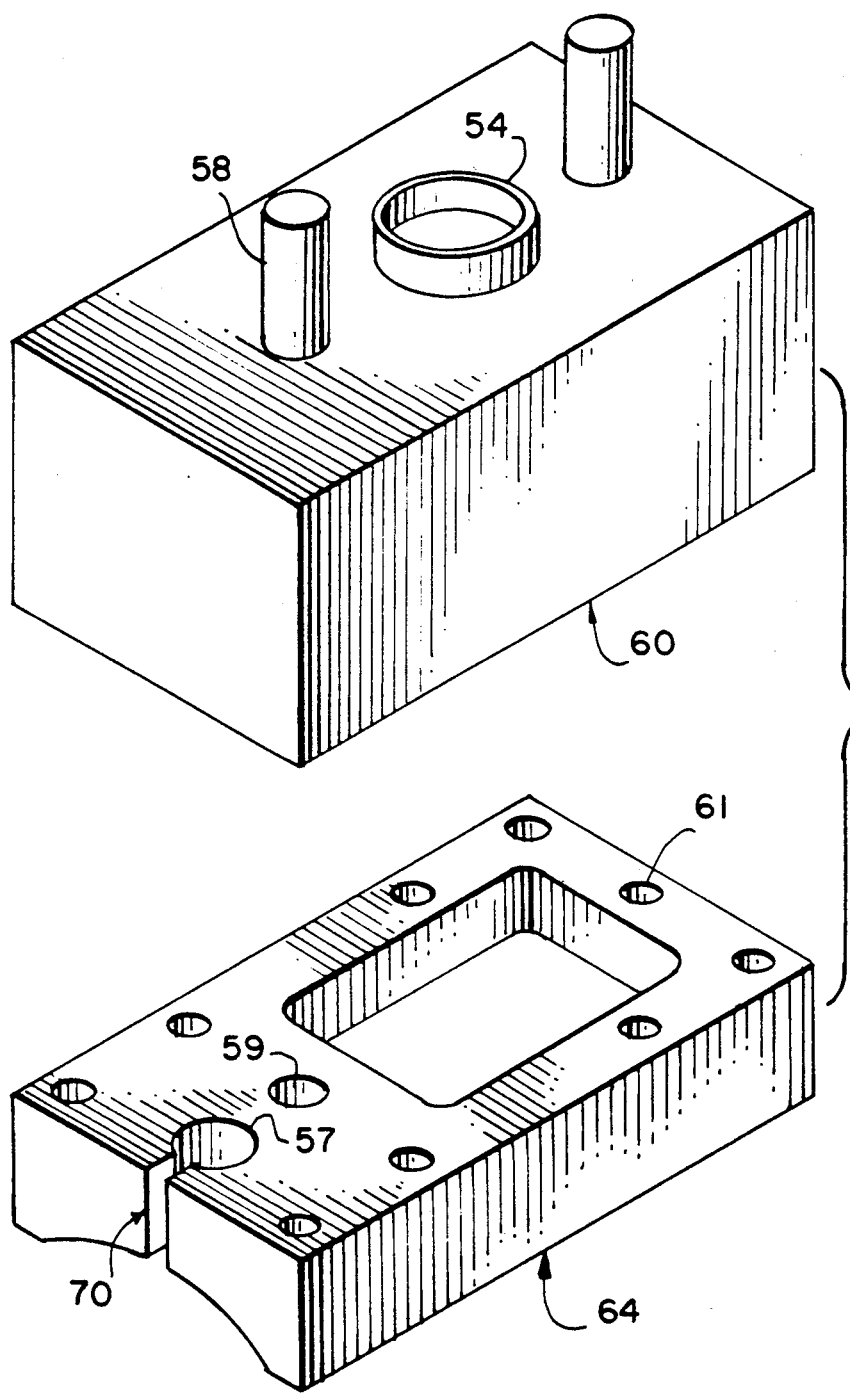
FIG. 7 is a partially exploded view of the probe unit of the flash gauge shown in FIG. 4.

Referring now to FIG. 7, an partial exploded view of the probe unit 12 is shown. A probe casing 60 is provided in which the probe control circuitry is contained and protected from environmental conditions. The casing 60 is also made from a material that will provide electromagnetic shielding for the probe control circuitry. The water inlet tubes 56 and 58 pass through the probe casing 60. A removable shoe 64 is attached to the bottom of the probe casing 60. The shoe 64 is contoured to fit the particular dimensions of the pipe to be tested. Thus, the probe unit 12 may be readily adapted for use with a variety of pipe products by replacing the removable shoe 64.

Figure 8:
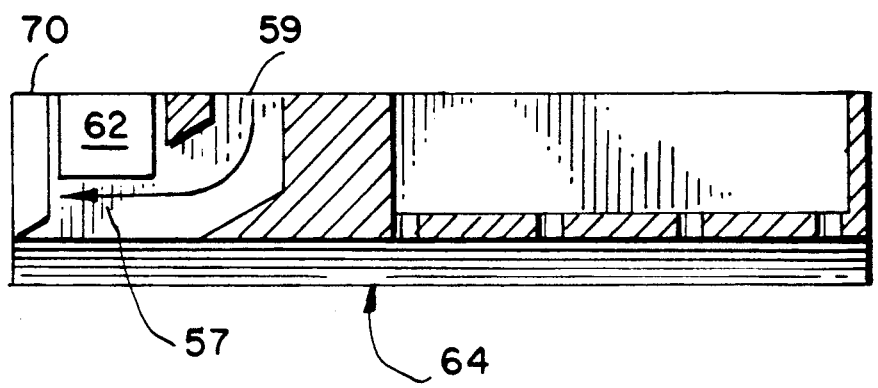
FIG. 8 is a cross sectional view of a probe show of the probe unit shown in FIG. 7.
Figure 9:
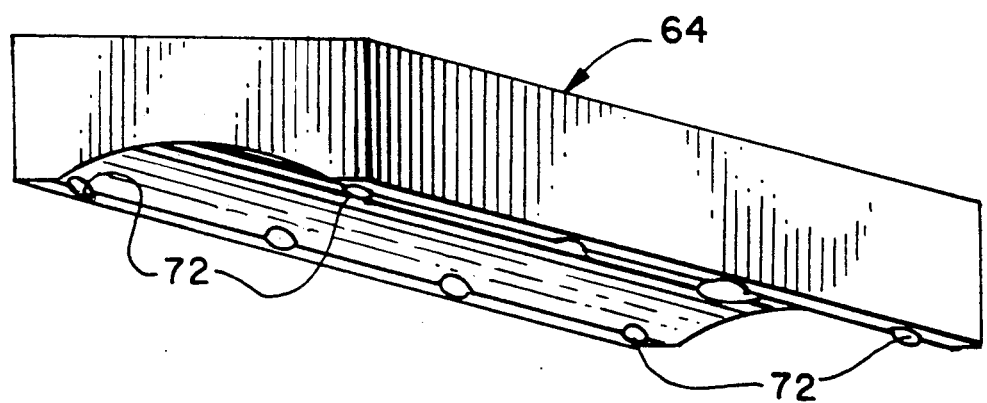
FIG. 9 is a perspective view of the face of the probe shoe shown in FIG. 8.

A more detailed description of the shoe 64 will now be made with reference to FIG. 8 which illustrates a cross-section of the shoe 64. The primary water inlet tube 58 protrudes into a primary water outlet port 59 which provides water flow across the face of an ultrasonic transducer 62 positioned in a transducer cavity 57 formed at one end of the shoe 64. The secondary water inlet tube 56 protrudes into a secondary water outlet port 61 located at the other end of the shoe 64. As previously stated, a water column is provided to acoustically couple the ultrasonic transducer 62 to the surface of the pipe being tested. The maintenance of a proper water column is important to the operation of the present invention. Water is pumped rapidly via the water inlet tube 58 to the primary water outlet port 59 across the face of the ultrasonic transducer 62 in the direction of the arrow as shown in FIG. 8. It is highly desirable to locate the flash gauge as close as possible to the welding operation. The high temperature of the weld seam, however, would normally cause boiling or bubbling of the water column which would disrupt the operation of the ultrasonic transducer. Various attempts to overcome this problem include the use of a large exit opening for the water flow in order to encourage rapid water flow to thereby prevent boiling. A large exit opening proved unsuccessful in overcoming the problem, as the opening actually encouraged the formation of air bubbles in the water column by creating a vacuum effect that sucked air into the opening. It was found that the use of a small tapered exit opening 70 (see FIG. 7) solved the problem of boiling and bubble formation. The width of the exit opening is typically about 0.080 to 0.100 inches. The small opening prevents air from being sucked into the transducer cavity 57 by providing sufficient back pressure, while the tapering provides smooth low turbulence flow which inhibits the formation of air bubbles. Thus, the water column can be maintained uniformly to prevent interference with the operation of the transducer 62. The optional secondary water outlet port 61 provides cooling of the shoe 64 and the probe unit 12, while at the same time providing a water lubrication layer between the probe shoe 64 and the pipe. It is noted that the curvature of the shoe 64 also must closely match the shape of the pipe being tested in order to avoid a large gap from being formed between the shoe 64 and the pipe. If the gap is too large, the water will flow from the sides of the shoe and boiling problems can occur. Proper gap spacing, preferably 0.015 to 0.025 on an inch, is maintained by wear inserts 72 provided on the bottom of the shoe 64 as shown in FIG. 9. The wear inserts 72 consist preferably of tungsten carbide or a ceramic material having a low coefficient of friction. The wear inserts 72 prevent premature wearing of the shoe 64 which is preferably made of aluminum or plastic. In a preferred embodiment four wear buttons 72 are provided, one on each corner of the shoe 64.

Figure 10:
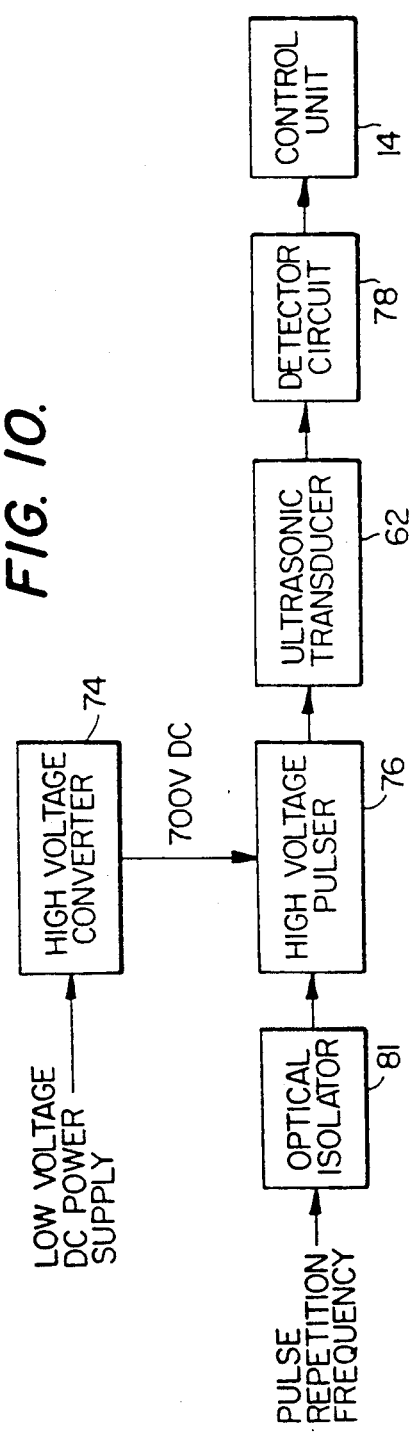
FIG. 10 is a block diagram of the probe control circuitry employed in the flash gauge shown in FIG. 4.
Figure 11:
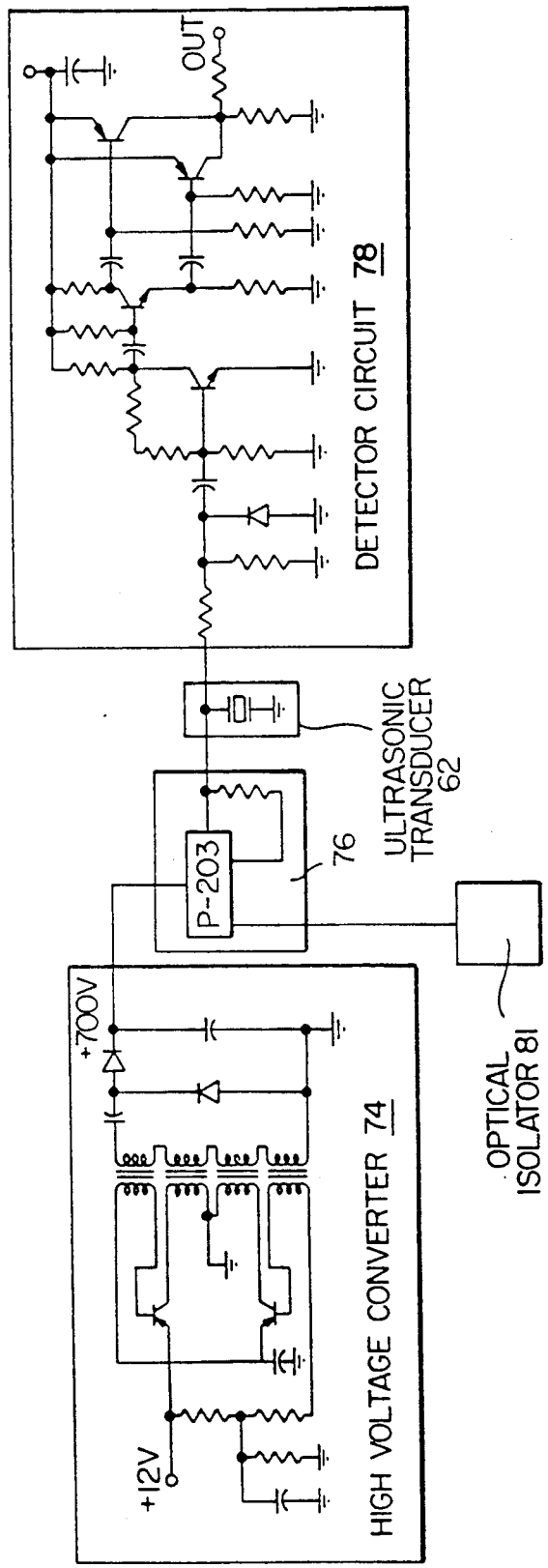
FIG. 11 is a detailed schematic diagram of the probe control circuitry illustrated in FIG. 10.

The electrical system for the invention will now be described with reference first to FIG. 10 which shows a block diagram of the probe control circuitry. The probe control circuitry consists of a high voltage converter circuit 74, a high voltage pulsar 76 connected to the ultrasonic transducer 62, and an amplifier circuit 78 for amplifying the signal received from the ultrasonic transducer. The high voltage converter circuit 74 steps up the voltage from 12 VDC into 700 volts. The 700 volt output from the converter circuit 74 is supplied to the voltage pulsar 76 which consists of a MetroTek Inc. Pulsar Module P-203. The voltage pulsar 76 outputs a sharp voltage pulse having an amplitude of 230 volts and a rise time of typically seven nanoseconds, upon receipt of the PRF signal from the control unit 14. The sharp voltage pulse is required in order to cause the transducer 62 to generate a single sound pulse, as the transducer 62 is highly damped to prevent ringing. Preferably an optical isolator 81 is provided to isolate the control unit 14 from the voltage pulsar circuit 76. The amplifier circuit 78 is a two stage amplifier that amplifies the voltage and current of the signal received from the ultrasonic transducer and outputs the amplified signal to the control unit 14. A detailed schematic diagram of the probe control circuitry is shown in FIG. 11.

As previously mentioned, the high resolution requirements for the detection of inside flash require a focused transducer. There are two common types of focused transducers; cylindrical and spherical. In a preferred embodiment, a cylindrically focused transducer is employed which has been found to produce the most satisfactory results, especially in thick wall pipes (over 0.100 in thickness). Spherically focused transducers may be employed in applications involving thin wall pipes (less than 0.100 in thickness). The cylindrical focused ultrasonic transducer 62 is heavily damped in order to permit the pulsar circuit 76 to function properly. As a result, the ultrasonic transducer 62 generates short broad band pulses offering high resolution. The frequency of operation of the ultrasonic transducer 62 is chosen to increase the resolving power of the flash gauge and for most applications is in the range of 10-20 Mhz. Additionally, the detection of high resolution flaws requires a specified beam shape. The transducer diameter is chosen according to the near field length of the probe which is not less than the expected flaw depth. An optimal focal length depends on pipe thickness, but a degree of compensation can be provided by varying the length of the water column between the transducer and the pipe. It has been found that typical focal lengths of about 0.5-1.5 inches and water column heights of about 0.125-0.750 inches provide the best results.

Figure 12:
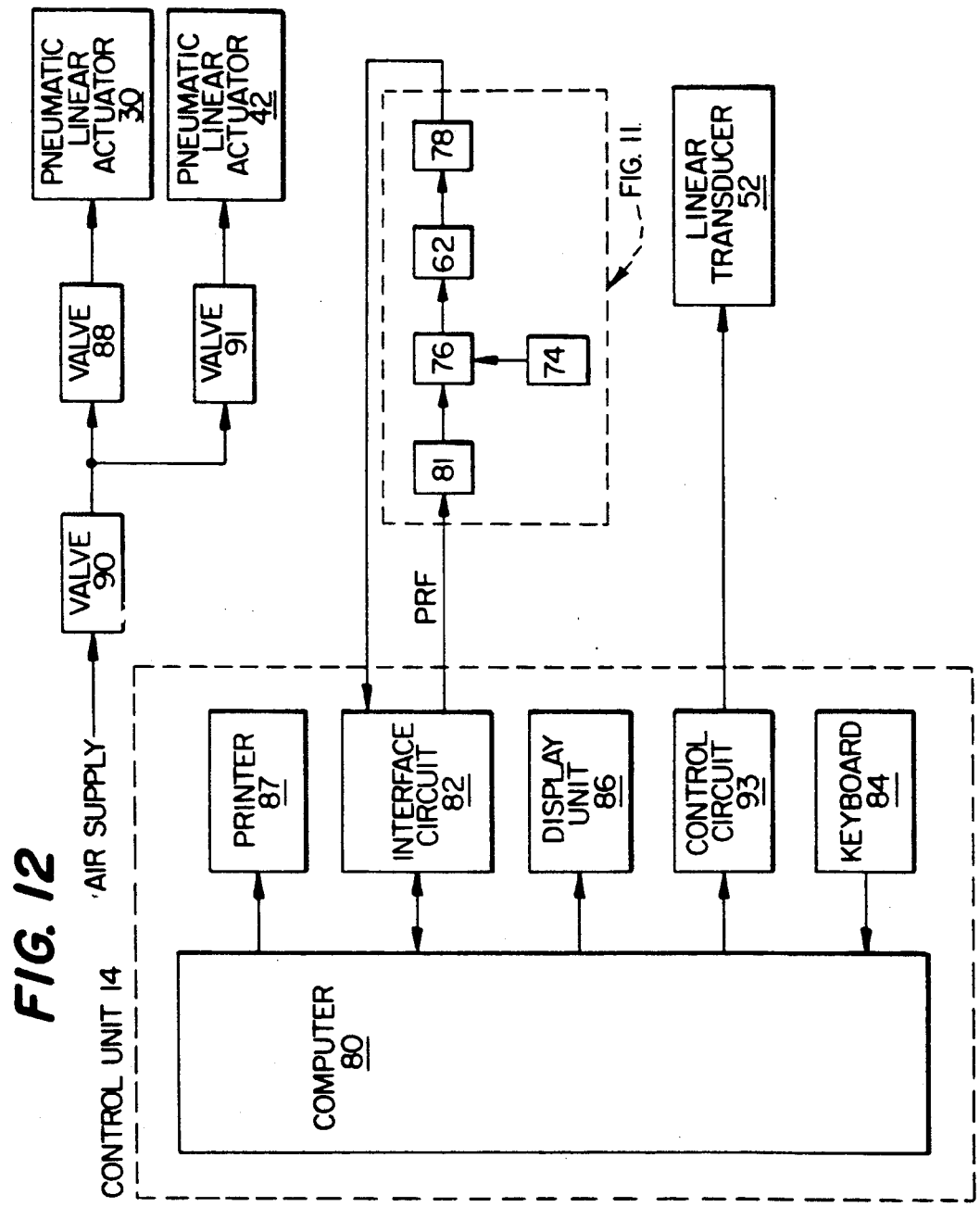
FIG. 12 is a functional block diagram of the flash gauge illustrated in FIG. 4.

A description of the overall operation of the flash gauge will now be made with reference to FIG. 12. The control unit 14, consists of a computer 80, interface circuit 82, keyboard 84, and display unit 86. An operator inputs, via the keyboard 84, inside flash limit values that the computer 80 uses to set-up reject and warning levels for out of range conditions. The operator also inputs a desired pulse repetition rate as well. Typically, the pulse repetition rate is set between 500-2000 with a stroke length of 0.5 to 2 inches for the probe unit transverse movement. It will be readily understood that these are typical values and can be varied depending on the particular application and desired resolution. The operator activates a pressure control valve 88 that provides air pressure to the pneumatic linear actuator 30 in order to move the control arm 26 to the horizontal position. The air pressure is maintained to the linear actuator 30 at a level to provide a downward load of approximately five pounds on the probe unit 12. The operator then activates a second pressure control valve 90 that supplies air pressure to the solenoid switching valve 91. The solenoid switching valve 91 alternately switches the air pressure in the double acting cylinder of the linear actuator 42, thereby causing oscillatory motion of the control arm 26. A control circuit 93 for the solenoid switching valve, located in the control unit 14, receives the output of the linear transducer in order to control the stroke length of the rod 44. The control unit 14 initiates scanning of the pipe by generating the PRF signal which is supplied to the high voltage pulsar 76. The high voltage pulsar outputs a single drive pulse for each PRF signal received from the control unit 14. The drive pulse is supplied to the ultrasonic transducer 62 causing it to generate a single sound pulse for every drive pulse received. Reflected signals received by the transducer 62 are supplied to the amplifier circuit 78 which returns the amplified signal to the control unit 14 for analysis.

Figure 13:
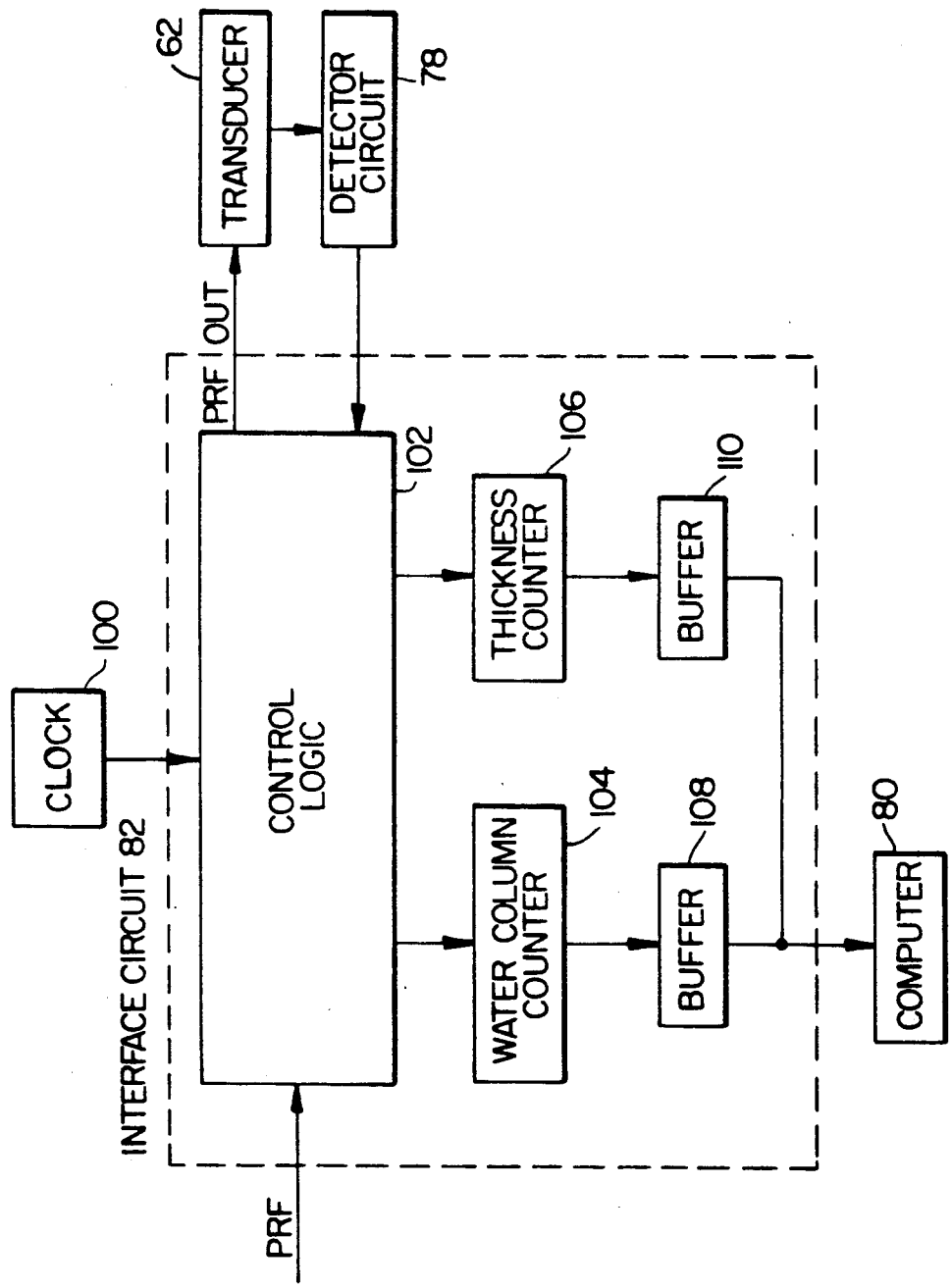
FIG. 13 is a block diagram of the interface circuit shown in FIG. 12.

A more detailed discussion of the operation of the control unit will now be made with reference first to FIG. 13 which shows a block diagram of the interface circuit 82. The interface circuit includes a clock 100, control logic 102, water column (WC) counter 104, wall thickness counter 106, and data buffers 108 and 110. The interface circuit receives a PRF signal from the computer 80 which is synchronized to the clock signal (typically 60-115 Mhz) generated by clock 100 by a delay circuit in the control logic 102. The control logic then transmits the PRF OUT signal to the ultrasonic transducer 62. The amplifier circuit detects the transmission of the PRF OUT signal as the amplifier circuit is connected to the point at which the PRF OUT signal is supplied to the transducer 62 (see for example FIG. 9). This causes the amplifier circuit to generate a first signal pulse which is returned to the control logic 102. The control logic 102 uses the first signal pulse received from the amplifier circuit to initialize the WC counter 104 and the TH counter 106.

Figure 14:
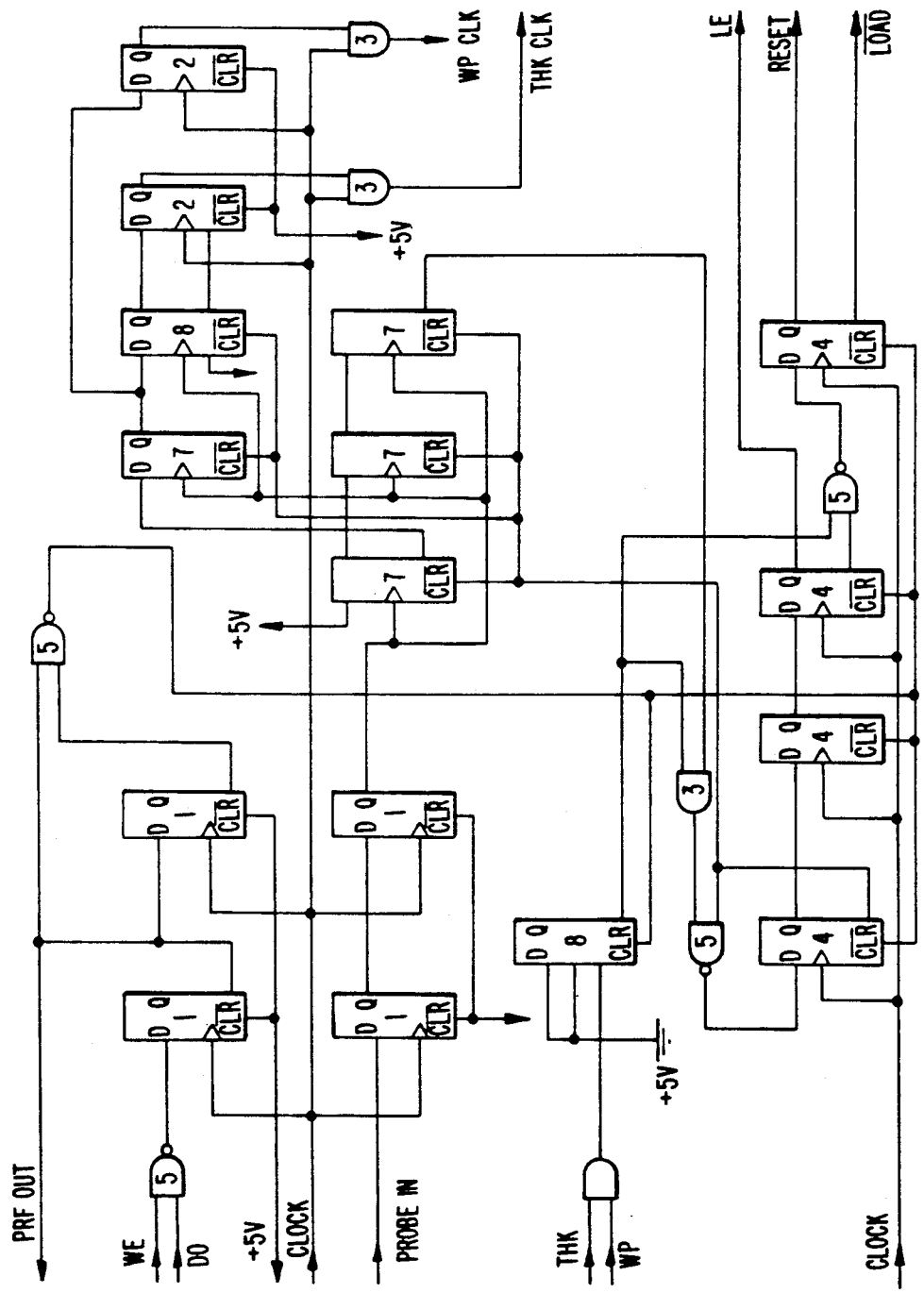
FIG. 14 is a detailed schematic diagram of the control logic for the interface circuit shown in FIG. 13.
Figure 15A:
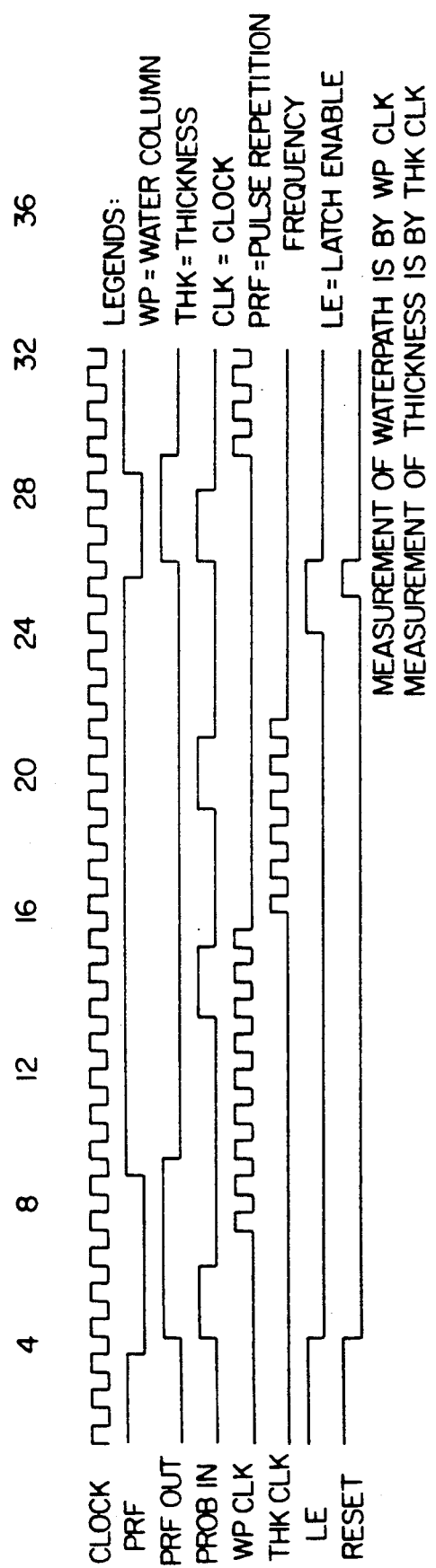
FIG. 15a is a timing diagram for the control logic circuit shown in FIG. 14 and 15b is a graph illustrating the operation of the logic circuit of FIG. 14.
Figure 15B:
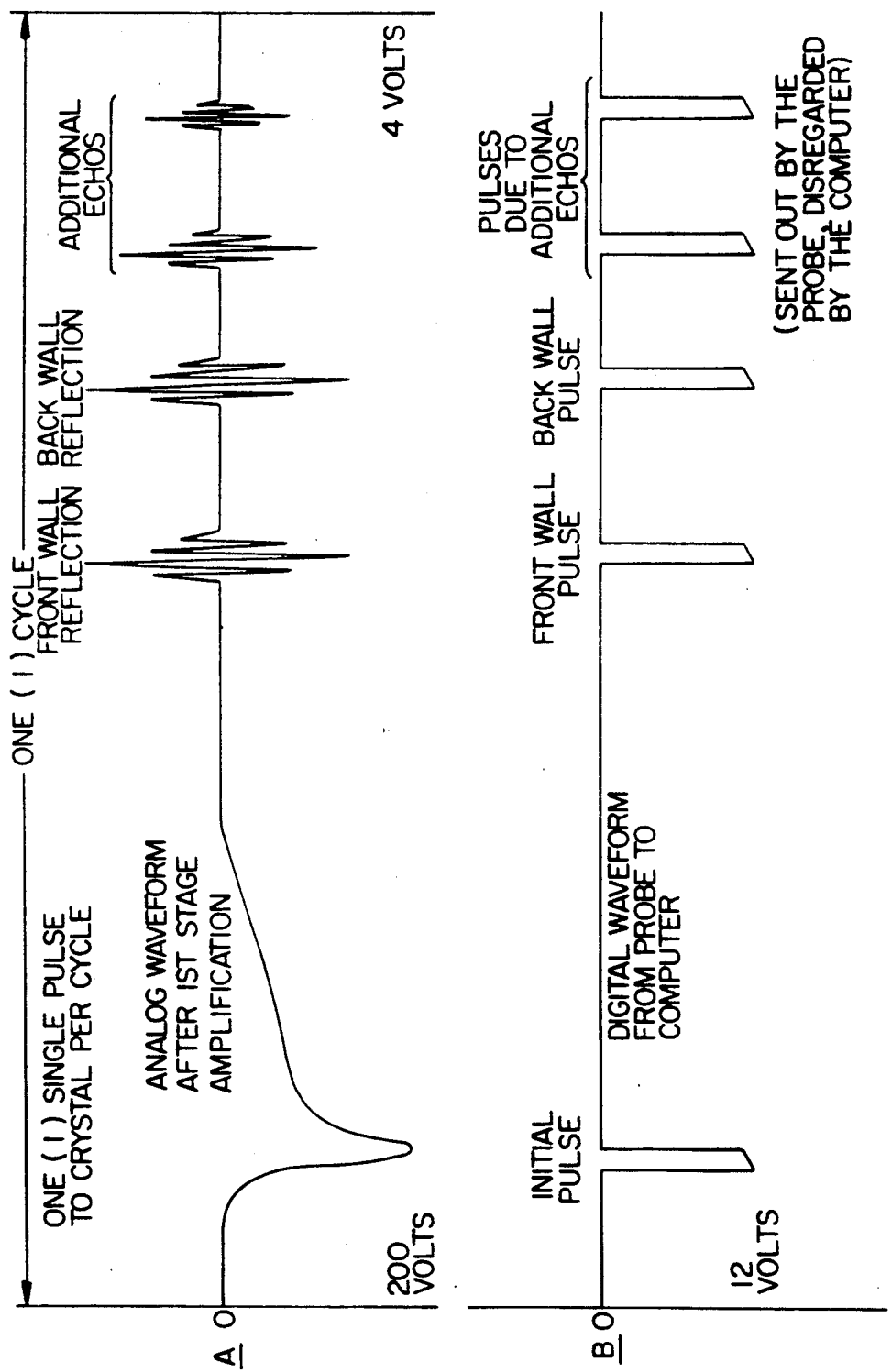

The ultrasonic transducer 62 generates a single sound pulse that is transmitted through the water column and pipe, and receives echo signals from the outside surface (front wall) and inside surface (back wall) of the pipe. The amplifier circuit detects the echo signals, and returns the amplified echo signals to the control logic 102. The logic circuit 102 generates a WP clock signal that increments the WC counter from the initialization point to the reception of the front wall echo signal. Similarly, the logic circuit 102 generates a TH clock signal that increments TH counter 106 from the reception of the front wall echo signal until the reception of the back wall echo signal. The count value of each counter 104, 106 is then stored in the buffers 108 and 110. A detailed schematic diagram of the control logic 102 is shown in FIG. 14. FIG. 15a is a timing diagram for the circuit shown in FIG. 14 and FIG. 15b is a graph illustrating the transmission of pulses and the receipt of signals.

The computer 80 then downloads the count values from the buffers 108 and 110 and displays the count values directly on the display unit or printer. Instead of direct display of the count values, the control unit 14 can calculate the actual thickness of the section of pipe being tested based on known ultrasonic transmission character------s for various pipe materials and the count values.         ant values representing the time interval measur.       -een receipt of a reflection signal from the outside s.   ...e of the pipe and the inside surface of the pipe. The computer 80 may also be employed to generate and display a graphical representation of the weld profile based on the count values.

Figure 16A:
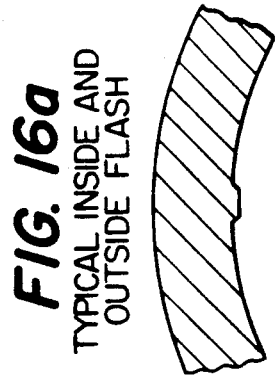
Figure 16B:
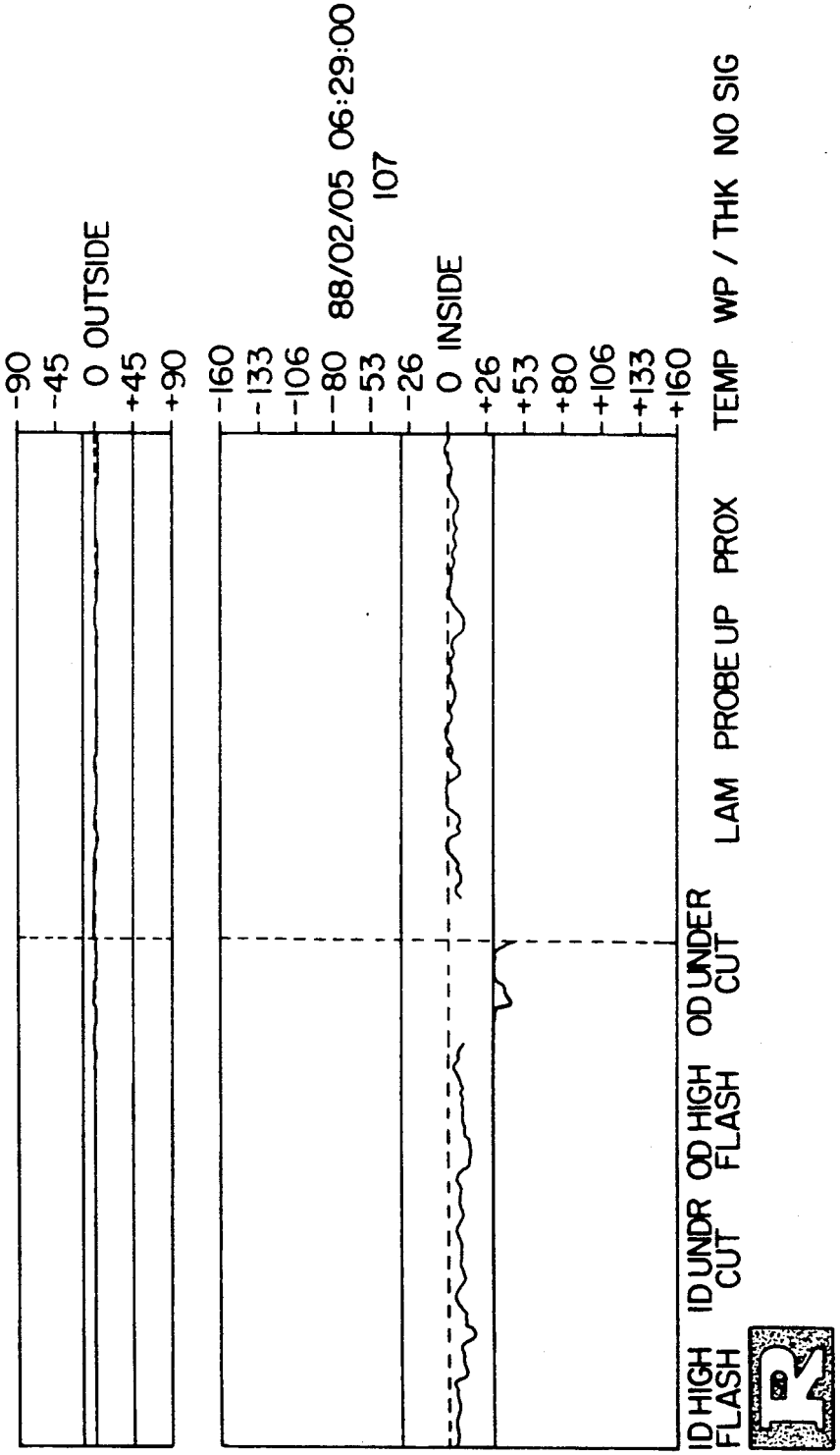
Figure 17A:
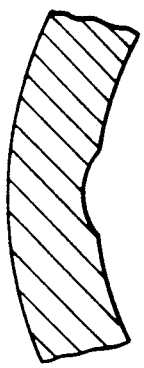
Figure 17B:
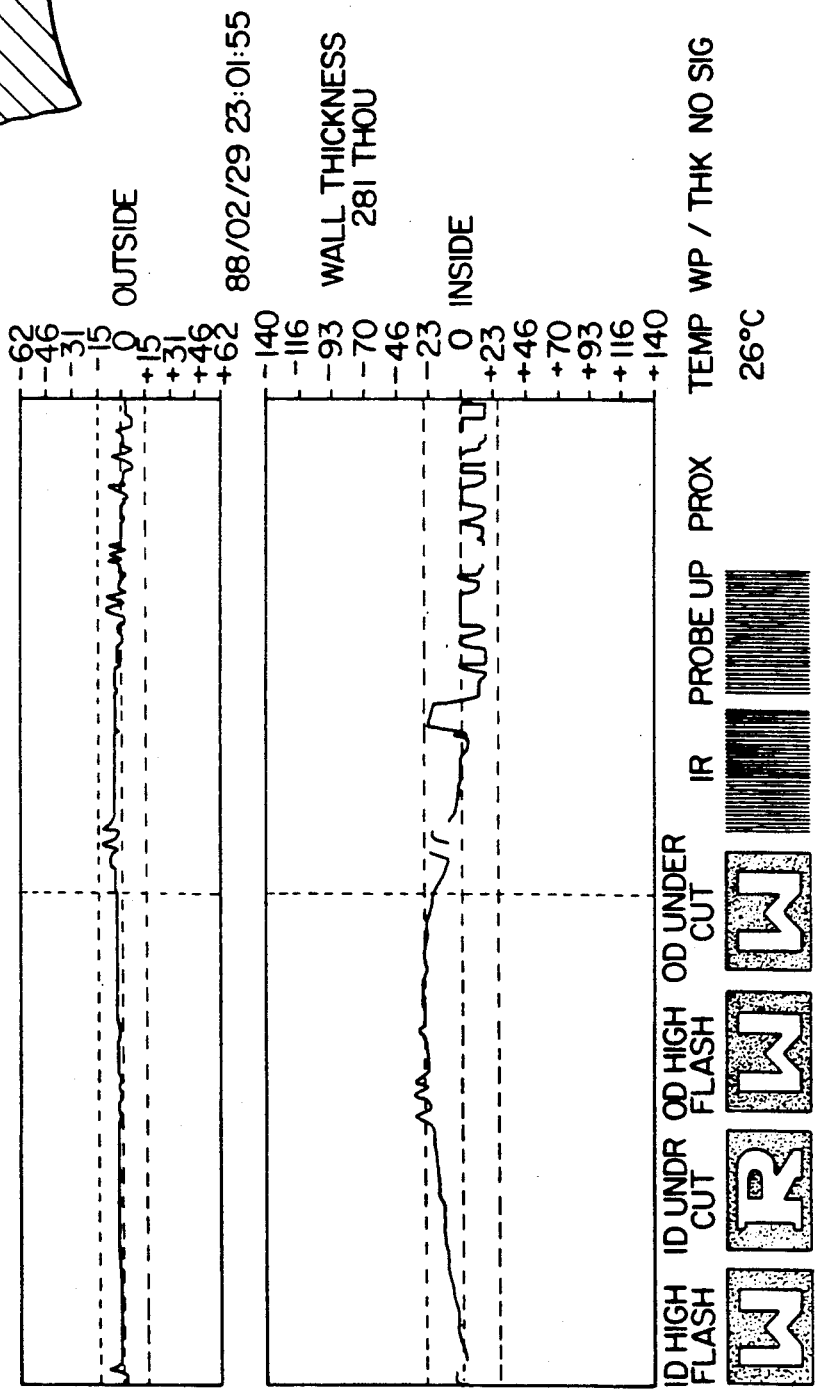

A preferred graphical representation is illustrated in the simulated displays shown in FIGS. 6-19 for various flash conditions. A graph is displayed on the display unit 86 which shows relative deviations from the desired thickness level for the pipe. The horizontal X-axis indicates the inside wall of the pipe and the vertical Y-axis indicates the center point of the weld. As indicated in FIGS. 16a-16b, inside flash is displayed in the positive direction of the Y-axis. FIGS. 17a-17b show the display of an undercut condition. The preferred display makes is easy for the operator to quickly and easily ascertain problems with the flash trimming process. For example, a grossly misaligned inside flash trim tool can cause excessive cutting into the wall of the pipe while leaving untrimmed flash behind as shown in FIG. 18a. This condition, however, can be quickly ascertained from the display shown in FIG. 18b. Similarly, a chipped inside flash trim tool can leave a condition as shown in FIG. 19a which can be readily ascertained from the display shown in FIG. 19b.

Figure 20:
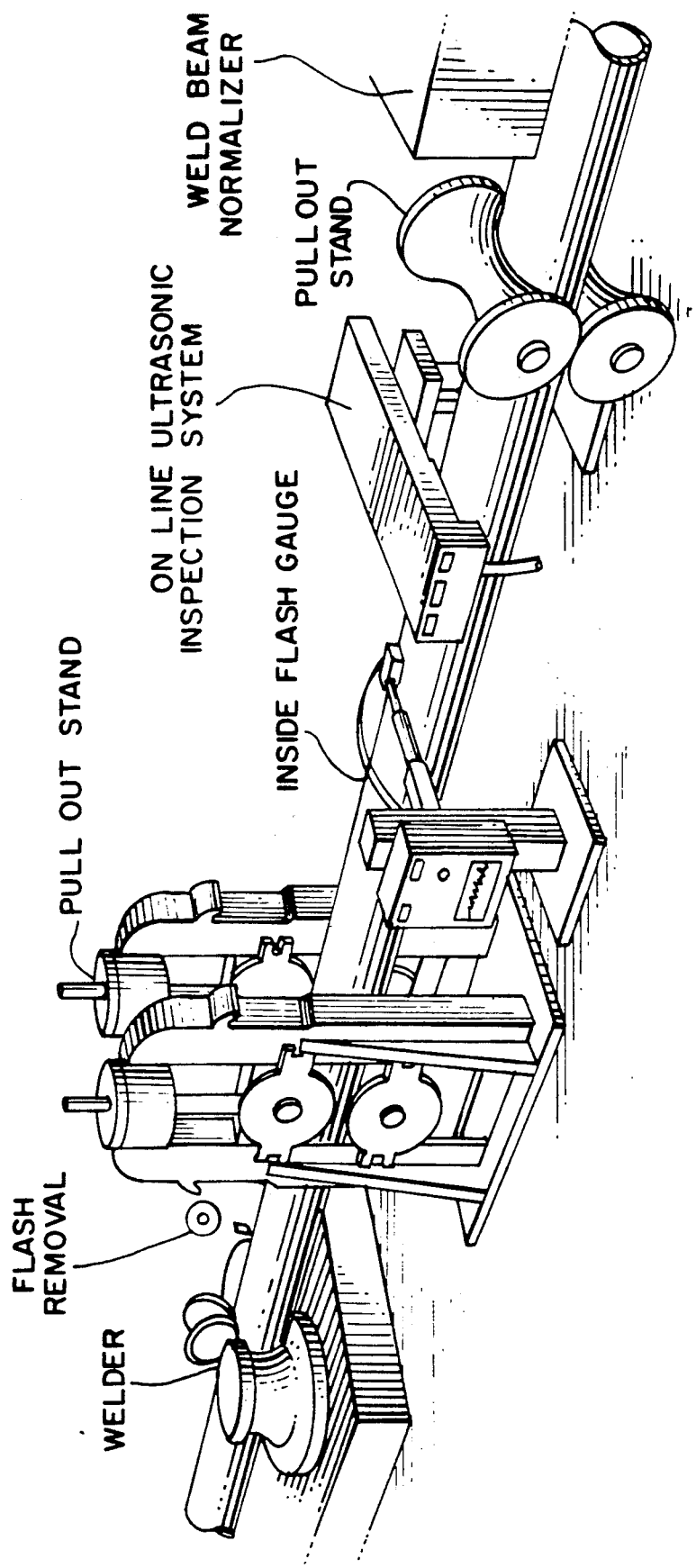
FIG. 20 illustrates the flash gauge shown in FIG. 4 employed in a continuous pipe production operation.

FIG. 20 illustrates the flash gauge incorporated in continuous tube production operation. The flash gauge is located as close as possible to the electric resistance welder. The temperature of the weld point, therefore, can approach 1500 degrees Fahrenheit. The shoe of the probe unit, however, is capable of preventing the water column from boiling and thereby interfering with the ultrasonic transducer. Monitoring of the weld point is, for all practical purposes, in real time, allowing the operator to instantaneously correct for any out of range.

The invention has been described in detail with particular reference to preferred embodiments thereof, but it will be understood that variations and modification can be effected within the spirit and scope of the invention. A temperature sensor may be employed to prevent the probe unit 12 from becoming overheated, which may cause possible damage to the probe control circuitry and the ultrasonic transducer. Additionally, the probe control circuitry may be located at a remote location from the probe unit 12 in order to reduce the overall size of the probe unit. The flash gauge may also be fully automated by having the control unit control the operation of the pressure regulating valves 88 and 90. Finally, the particular size and shape of the exit opening may be varied while maintaining the primary purpose of the exit opening.

What is claimed is:

1. An apparatus for detecting inside flash, said apparatus comprising:
   a. a probe unit having a focused ultrasonic transducer, for generating a signal indicative of the thickness of a weld point on a material to be tested, said transducer being spaced from said weld point by a water column, and said probe unit including a primary water inlet tube that provides a path for water to flow to a primary water outlet port, said primary water outlet port providing a path for water to flow past the face of said ultrasonic transducer and out an exit path to thereby prevent entrapment of air bubbles or boiling of the water column during operation of said focused ultrasonic transducer;
   b. a positioning unit for maintaining the horizontal and vertical position of said probe unit relative to said weld area;
   c. control circuitry for controlling the operation of said probe unit and for displaying the signal generated by said probe unit, wherein said control circuitry comprises a control unit and a probe control circuit, said probe control circuit including a high voltage converter for converting a low voltage input signal to a high voltage output signal, a high voltage pulsar that receives said high voltage output signal and generates a signal pulse, when a control signal is received from said control unit, that is supplied to said ultrasonic transducer, and an amplifier circuit for receiving reflected signals from said ultrasonic transducer and generating an amplified signal that is returned to said control unit.

2. An apparatus as claimed in claim 1 wherein said probe unit comprises a housing and a removable shoe that contacts the surface of said material to be tested, said shoe being contoured to match the shape of said material to be tested.

3. An apparatus as claimed in claim 1 wherein said exit path is tapered.

4. An apparatus as claimed in claim 1 wherein said exit path is formed of a slot.

5. An apparatus as claimed in claim 4 wherein said slot has a width of a range of approximately 0.080-0.100 inches at the exit point of the water.

6. An apparatus as claimed in claim 2 wherein said shoe includes a plurality of wear inserts that separate the face of said shoe from said material to be tested.

7. An apparatus as claimed in claim 1 wherein said positioning unit comprises a support structure, a control arm coupled to said support structure, and an actuator for raising and lowering said control arm, said actuator providing a downward force on said probe unit.

8. An apparatus for detecting inside flash, said apparatus comprising:
   a. a probe unit having a focused ultrasonic transducer, for generating a signal indicative of the thickness of a weld point on a material to be tested, said transducer being spaced from said weld point by a water column, and said probe unit further comprising a primary water inlet tube that provides a path for water to flow to a primary water outlet port, said primary water outlet port providing a path for water to flow past the face of said ultrasonic transducer and out an exit path to thereby prevent entrapment of air bubbles or boiling of the water column during operation of the focused ultrasonic transducer;
   b. a positioning unit for maintaining the horizontal and vertical position of said probe unit relative to said weld area, said positioning unit comprising a support structure, a control arm coupled to said support structure, and an actuator for raising and lowering said control arm, said actuator providing a downward force on said probe unit;
   c. control circuitry for controlling the operation of said probe unit and for displaying the signal generated by said probe unit;
   wherein said control arm comprises a linear actuator coupled to said probe unit and a linear transducer for generating a signal indicative of the translational movement of said linear actuator, said linear actuator moving said probe unit in an oscillatory manner over said weld point.

9. An apparatus as claimed in claim 8, wherein said control circuitry receives the signal generated from said linear transducer and controls the operation of said linear actuator.

10. An apparatus as claimed in claim 9, wherein said linear actuator comprises a first rod rotatably coupled to a second rod which is connected to a piston.

11. An apparatus as claimed in claim 1, wherein said high voltage pulsar generates a signal pulse having an amplitude of about 230 volts and a rise time of about seven nanoseconds.

12. An apparatus as claimed in claim 1, wherein said ultrasonic transducer is a cylindrically focused transducer.

13. An apparatus for detecting inside flash, said apparatus comprising:
   a. transducer means for transmitting an ultrasonic sensing signal and receiving reflected signals;
   b. positioning means for positioning said transducer means relative to a weld line on a test material and moving said transducer means in an oscillatory manner in a direction transverse to said weld line;
   c. means for uniformly maintaining a water column between said transducer means and said test material in order to prevent entrapment of air bubbles or boiling of said water column during the operation of said transducer means, said means including water path means for providing a rapid flow of water across said transducer means;
   d. circuit means for controlling the operation of said transducer means and for receiving the reflected signals from said transducer means, said circuit means generating a signal indicative of the thickness of said test material; and
   e. display means for receiving and displaying said signal indicative of the thickness of said test material.

14. An apparatus as claimed in claim 13, wherein said transducer means comprises a focused ultrasonic transducer.

15. An apparatus as claimed in claim 14, wherein said focused ultrasonic transducer comprises a cylindrical focused transducer.

16. An apparatus as claimed in claim 13, wherein said means for maintaining a uniform water column comprises a probe shoe having means for providing a rapid flow of water past said transducer means while preventing the boiling of said water column high temperature conditions and the entrapment of air bubbles in said water column.

17. An apparatus as claimed in claim 13, wherein said circuit means comprises: means for converting a supplied low voltage to a high voltage, pulsar means for receiving said high voltage and generating a high voltage pulse signal having a rapid rise time, said high voltage pulse signal being supplied to said transducer means, and amplifier means for receiving and amplifying said reflected signals received by said transducer means.

18. An apparatus as claimed in claim 17, wherein said circuit means further comprises control means coupled to said amplifier means for generating a control signal that initiates the operation of said pulsar means, and for receiving said reflected signals that are amplified by said amplifier means.

19. An apparatus as claimed in claim 13, further comprising means for detecting an overtemperature condition of said transducer means.

20. An apparatus as claimed in claim 1 wherein said probe unit is capable of operating at weld point temperatures of about 1500 degrees Fahrenheit.

21. An apparatus as claimed in claim 7 wherein said control arm comprises a linear actuator coupled to said probe unit and a linear transducer for generating a signal indicative of the translational movement of said linear actuator, said linear actuator moving said probe unit in an oscillatory manner over said weld point.

22. An apparatus as claimed in claim 21, wherein said control circuitry receives the signal generated from said linear transducer and controls the operation of said linear actuator.

23. An apparatus as claimed in claim 22, wherein said linear actuator comprises a first rod rotatably coupled to a second rod which is connected to a piston.

24. An apparatus as claimed in claim 8 wherein said probe unit comprises a housing and a removable shoe that contacts the surface of said material to be tested, said shoe being contoured to match the shape of said material to be tested.

25. An apparatus as claimed in claim 8 wherein said exit path is tapered.

26. An apparatus as claimed in claim 8 wherein said exit path is formed by a slot.

27. An apparatus as claimed in claim 26 wherein said slot has a width of a range of approximately 0.080–0.100 inches at the exit point of the water.

28. An apparatus as claimed in claim 24 wherein said shoe includes a plurality of wear inserts that separate the face of said shoe from said material to be tested.

29. An apparatus as claimed in claim 8, wherein said probe unit is capable of operating at weld point temperatures of about 1500 degrees Fahrenheit.

* * * * *